United States Patent
Kyriakou

(10) Patent No.: US 9,218,658 B2
(45) Date of Patent: Dec. 22, 2015

(54) METHOD FOR DETERMINING AN ARTIFACT-REDUCED THREE-DIMENSIONAL IMAGE DATA SET AND X-RAY DEVICE

(71) Applicant: Yiannis Kyriakou, Spardorf (DE)

(72) Inventor: Yiannis Kyriakou, Spardorf (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 170 days.

(21) Appl. No.: 13/847,614

(22) Filed: Mar. 20, 2013

(65) Prior Publication Data

US 2013/0259355 A1 Oct. 3, 2013

(30) Foreign Application Priority Data

Mar. 30, 2012 (DE) .......................... 10 2012 205 222

(51) Int. Cl.

| | | |
|---|---|---|
| G06K 9/00 | (2006.01) | |
| G06T 7/00 | (2006.01) | |
| G06T 5/00 | (2006.01) | |
| G06T 5/50 | (2006.01) | |
| A61B 6/00 | (2006.01) | |

(52) U.S. Cl.
CPC .............. G06T 7/0012 (2013.01); A61B 6/5258 (2013.01); G06T 5/005 (2013.01); G06T 5/50 (2013.01); G06T 2207/10116 (2013.01); G06T 2207/20221 (2013.01); G06T 2207/20224 (2013.01); G06T 2207/30016 (2013.01)

(58) Field of Classification Search
None
See application file for complete search history.

(56) References Cited

U.S. PATENT DOCUMENTS

| | | | | |
|---|---|---|---|---|
| 6,125,193 | A * | 9/2000 | Han .............................. | 382/131 |
| 6,690,371 | B1 * | 2/2004 | Okerlund et al. ............ | 345/424 |
| 8,718,346 | B2 * | 5/2014 | Isaacs et al. .................. | 382/131 |
| 9,036,886 | B2 * | 5/2015 | Hsieh et al. .................... | 382/131 |
| 2004/0146136 | A1 * | 7/2004 | Gringauz et al. ................ | 378/4 |
| 2005/0165292 | A1 * | 7/2005 | Simon et al. .................. | 600/407 |
| 2005/0238133 | A1 * | 10/2005 | Koppe et al. ...................... | 378/4 |
| 2006/0239585 | A1 * | 10/2006 | Valadez et al. ................ | 382/275 |
| 2006/0285737 | A1 * | 12/2006 | Hamill et al. ................. | 382/131 |
| 2008/0219534 | A1 * | 9/2008 | Faul et al. ..................... | 382/131 |

(Continued)

FOREIGN PATENT DOCUMENTS

| | | |
|---|---|---|
| DE | 19515550 A1 | 10/1996 |
| DE | 102008050570 A1 | 4/2010 |

OTHER PUBLICATIONS

M. Bal and L. Spies. "Metal artifact reduction in CT using tissue-class modeling and adaptive prefiltering", Med. Phys. 33(8), Aug. 2006, pp. 2852-2859.*

(Continued)

*Primary Examiner* — Vu Le
*Assistant Examiner* — Samah Beg

(57) ABSTRACT

A method of determining an artifact-reduced three-dimensional reconstructed image data set includes a plurality of projection images of a primary data set, which show a head of a patient together with at least one neurosurgical apparatus generating artifacts in a three-dimensional reconstruction. The projection images of the primary data set are captured using different projection directions by an X-ray device having a C-arm. With regard to a reduction of artifacts, a projection image based correction is based upon projection images of a mask data set which show the neurosurgical apparatus without the head of the patient or the head of the patient without the neurosurgical apparatus.

16 Claims, 3 Drawing Sheets

(56) References Cited

U.S. PATENT DOCUMENTS

| | | | |
|---|---|---|---|
| 2008/0247503 A1* | 10/2008 | Lauritsch et al. | 378/4 |
| 2008/0292157 A1* | 11/2008 | Forthmann et al. | 382/128 |
| 2009/0074278 A1* | 3/2009 | Beaulieu et al. | 382/131 |
| 2010/0061610 A1* | 3/2010 | Van De Haar | 382/131 |
| 2010/0286995 A1* | 11/2010 | Pekar et al. | 705/2 |
| 2011/0007980 A1* | 1/2011 | Fahimian et al. | 382/254 |
| 2011/0013742 A1* | 1/2011 | Zaiki et al. | 378/15 |
| 2011/0013817 A1* | 1/2011 | Medow | 382/131 |
| 2011/0081071 A1* | 4/2011 | Benson et al. | 382/154 |
| 2011/0206258 A1* | 8/2011 | Chen et al. | 382/131 |
| 2012/0294501 A1* | 11/2012 | Kyriakou | 382/131 |
| 2012/0294504 A1* | 11/2012 | Kyriakou | 382/132 |
| 2013/0039556 A1* | 2/2013 | Kachelriess et al. | 382/131 |
| 2013/0188771 A1* | 7/2013 | Kyriakou | 378/19 |
| 2013/0188848 A1* | 7/2013 | Helm et al. | 382/131 |
| 2014/0073907 A1* | 3/2014 | Kumar et al. | 600/414 |
| 2014/0149929 A1* | 5/2014 | Barnhorst et al. | 715/799 |
| 2015/0078507 A1* | 3/2015 | Kyriakou | 378/4 |
| 2015/0092907 A1* | 4/2015 | Dong et al. | 378/4 |

OTHER PUBLICATIONS

Wei et al. "X-ray CT high-density artefact suppression in cryosurgery," Phys Med Biol. 47 (2002), p. 319-326.*

Baissalov et al. "Suppression of high-density artefacts in x-ray CT images using temporal digital subtraction with application to cryotherapy," Phys Med Biol 45 (2000), p. 53-59.*

A. Sharan and D. Andrews, "Stereotactic Frames: Technical Considerations," Handbook of Stereotactic and Functional Neurosurgery, 2003, Chapter 2, p. 11-12.*

* cited by examiner

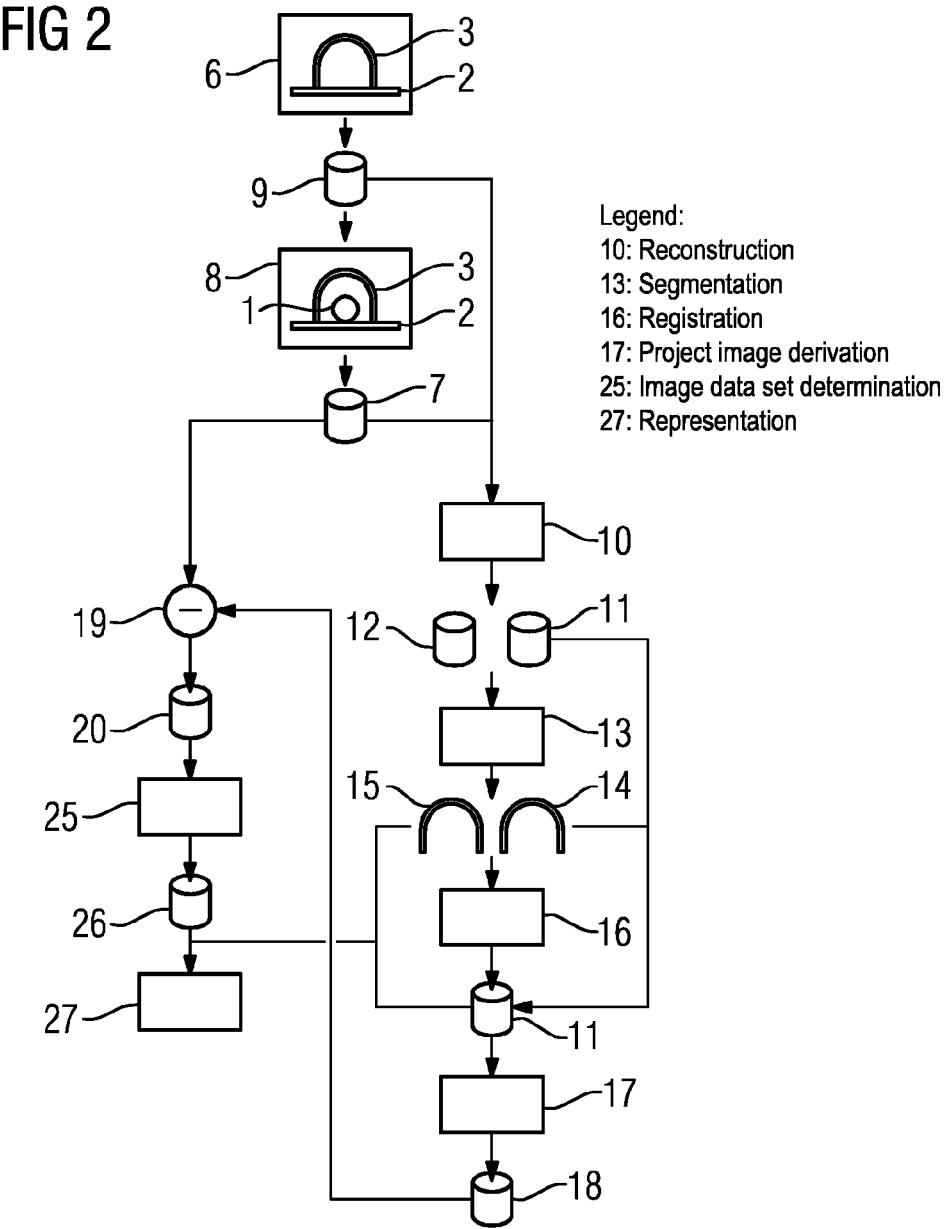

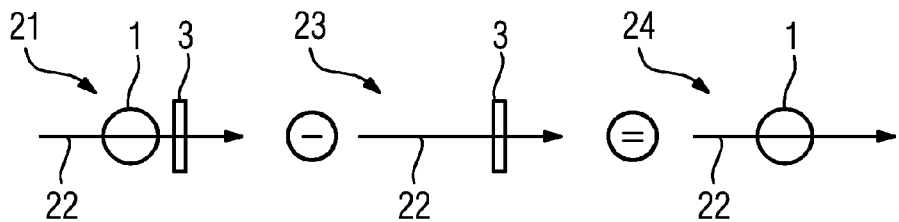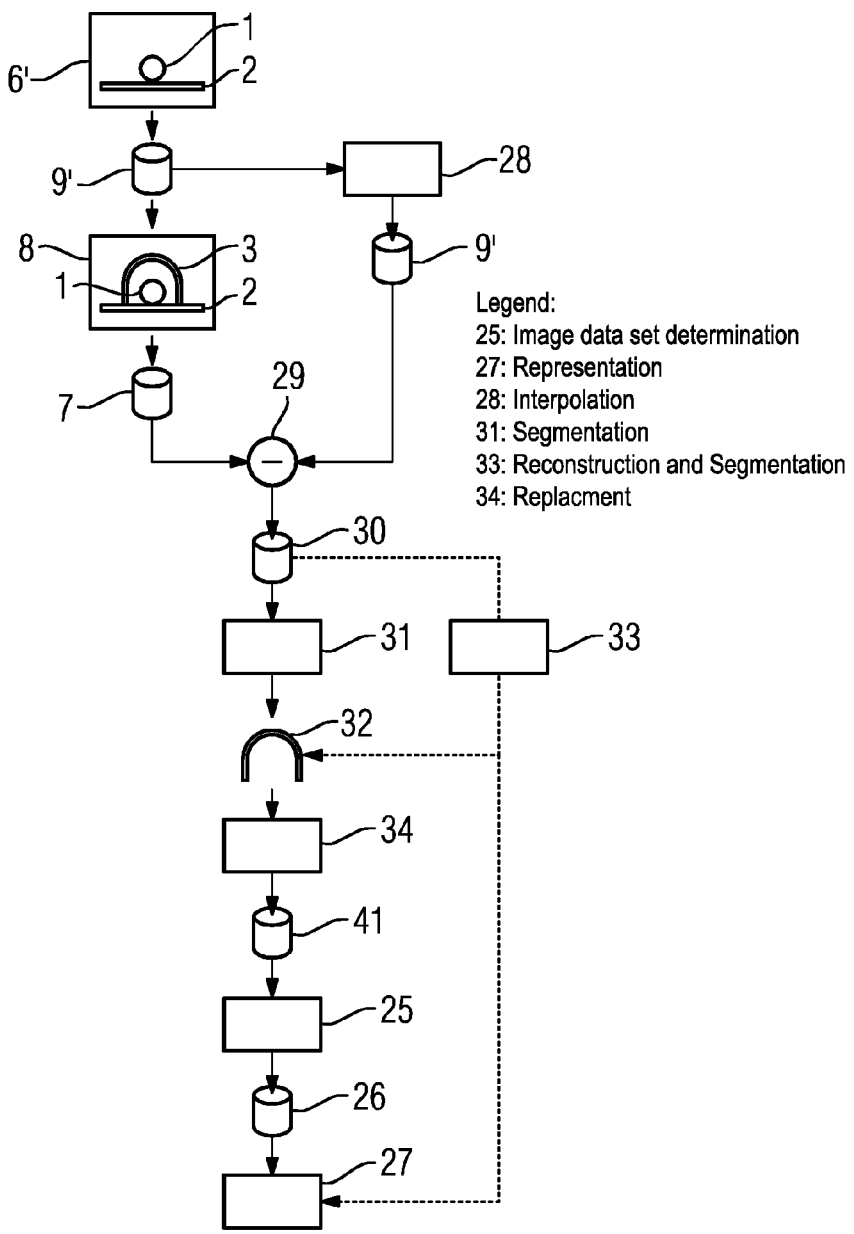

METHOD FOR DETERMINING AN ARTIFACT-REDUCED THREE-DIMENSIONAL IMAGE DATA SET AND X-RAY DEVICE

CROSS REFERENCE TO RELATED APPLICATIONS

This application claims priority of German Application No. 10 2012 205 222.4 DE filed Mar. 30, 2012. All of the applications are incorporated by reference herein in their entirety.

FIELD OF INVENTION

A method for determining an artifact-reduced three-dimensional image data set reconstructed taking into consideration a plurality of projection images of a primary data set which show a head of a patient together with at least one neurosurgical apparatus generating artifacts in the case of a three-dimensional reconstruction is provided, said projection images being captured using different projection directions by an X-ray device, in particular an X-ray device having a C-arm, and an X-ray device is provided.

BACKGROUND OF INVENTION

The generation of three-dimensional image data sets from two-dimensional projection images captured using different projection directions is already widely known and forms a basis for three-dimensional tomographic methods in computed tomography (CT). It has however also been proposed with increasing frequency in the context of interventions, in particular minimally invasive interventions, to utilize the advantages of available three-dimensional information, with the result that for example, CT-like methods have also been proposed for the generation of three-dimensional image data sets for X-ray devices having a C-arm which can be employed at a point of intervention, for example known under the name "DynaCT". In this situation, when the C-arm is rotated around the patient, projection images of the region of interest are captured using different projection directions, in other words different projection angles, from which projection images a three-dimensional reconstructed image data set can then be determined by means of known methods, for example analytical methods such as filtered back projection or iterative methods.

Problems occur with regard to such investigations for example in the situation when a supporting apparatus, in particular a stereotactic frame, is employed in the region of the neurosurgery. In this situation, the more general term of neurosurgical apparatus is intended to be understood in this description not only as a stereotactic frame in itself but in fact also to include other positioning aids, neurosurgical instruments, for example puncture needles, even also markers arranged for the most part on the patient, the instrument and/or the stereotactic frame, which are used for the registration of coordinate systems, for example by way of an optical tracking system. Stereotactic frames and/or other special apparatuses are used for guidance and execution in the case of a minimally invasive intervention, for example a puncture.

Should it then be intended to further support the intervention through the capture of a three-dimensional image data set, the neurosurgical apparatuses are situated completely or at least partially in the field of view of the X-ray device, in particular of an X-ray device having a C-arm. Because in particular frames and markers for the optical registration frequently consist of a very dense material, in particular exhibiting a high atomic number, they can cause artifacts in the image data sets. Although neurosurgical apparatuses which are improved in this respect, for example consisting of materials having a low atomic number, are also known, for example stereotactic frames made of carbon, these are however for the most part extremely expensive.

The typical workflow involved in capturing the image data set during a neurosurgical intervention is that the patient is positioned on a patient table and the neurosurgical apparatuses, in particular a stereotactic frame, are adjusted and fixed. Then the projection images are captured, for example during one rotation of the C-arm around the head of the patient. The captured projection images can for example be reconstructed using the Feldkamp algorithm to form the three-dimensional reconstructed image data set. The 3-D volume produced contains artifacts due to the neurosurgical apparatuses.

In order to eliminate these artifacts it is known to use metal artifact correction algorithms which in regions of strong attenuations, for example caused by metals, replace the image data with in particular linearly interpolated image data outside these regions. The use of beam hardening correction algorithms of an iterative nature has also already been proposed.

These approaches have the disadvantage that they are for the most part not suitable for handling effects of truncated projection images which in particular do not show the entire neurosurgical apparatus. Artifacts may remain or even be exacerbated. Furthermore, these algorithms depend on the quality of the projections and the segmentation, in particular the segmentation of regions to be interpolated because the segmentation is performed in the three-dimensional volume, in other words the uncorrected image data set. The algorithms have a strong noise dependence and can only be employed scarcely meaningfully in the case of low 3-D image quality since they operate in image-based fashion. A further disadvantage is the fact that the interpolation, in particular a linear interpolation, has too great an influence on the resolution and the image quality.

SUMMARY OF INVENTION

It is an object to specify a correction method which may be employed in particular both for truncated and also for non-truncated projection images and enhances the image quality of the image data set.

In order to achieve this object, a method of the type described in the introduction is provided, which, with regard to the reduction of the artifacts, a projection image based correction takes place taking into consideration projection image data of the projection images of a mask data set which show the neurosurgical apparatus without the head or the head without the neurosurgical apparatus.

A correction in the projection images is consequently proposed which is based on determining the attenuation components originating from the patient, thus specifically the head, by using a mask data set which shows either only the neurosurgical apparatus or only the head of the patient. By using a mask data set showing the neurosurgical apparatus, it is for example possible for portions of the attenuation values of the projection images originating from the neurosurgical apparatus to be removed in the primary data set, while in the other case the mask data set can ultimately be employed as a type of "attenuation map" for regions in which the neurosurgical apparatus is visible in the primary data set. In both cases it is therefore proposed to generate a comparison data set using comparison projection images which make it possible to ultimately remove the neurosurgical apparatus from the projection images and consequently to determine an image data set of the head alone.

Even if a stereotactic frame can for the most part be used as an example of a neurosurgical apparatus in the following, the term does however relate, as already explained in the introduction, to all apparatuses utilized in the context of neurosurgery which could be present in the imaging area, in particular therefore also to a surgical instrument and/or markers as components of an in particular optical tracking system or localization and registration system.

The described method has a multitude of advantages. In particular in comparison with methods which utilize an interpolation, measured data is used in order to avoid the artifacts occurring during the reconstruction on account of the neurosurgical apparatus, which contributes towards maintenance of the resolution and of the image quality. The proposal described here permits a correction of artifacts from the neurosurgical apparatus both for truncated and also for non-truncated data. The method is simple to use and to implement. Both capture operations, in other words that for the primary data set and that for the mask data set, can be carried out independently, and if an additional patient dose occurs this can be adjusted accordingly.

The correction proposed here based on the raw data exhibits a smaller dependence on the artifacts in the three-dimensional volume. The result is a largely artifact-free image data set of the head, in which case the method additionally allows, as will be described in more detail in the following, the neurosurgical apparatus itself to be segmented in three-dimensional form and to have this available in addition to the three-dimensional image data of the head.

In this situation it is particularly expedient if movements between the capture of the primary data set and of the mask data set are avoided as far as possible, which means it is advantageously provided that the head or the neurosurgical apparatus is held essentially motionless between the capture of the projection images of the mask data set and the capture of the projection images of the primary data set. If no appreciable movement whatsoever takes place it can be assumed that because the projection images already correspond to one another in their projection directions a registration naturally results, in which case in the event of smaller movements and/or adjustments a registration, which will be described in more detail in the following, can lead to a successful outcome in a particularly simple manner.

A first alternative embodiment is concerned with the capture only of the neurosurgical apparatus. Provision can thus be made that initially the mask data set of the neurosurgical apparatus in particular already adjusted to the head is captured, in which case after capture of the projection images of the primary data set, projection images, corresponding to one another in the projection directions, of the primary data set and of the mask data set, are subtracted from one another in order to determine subtraction images, in which case the image data set is reconstructed from the subtraction images. In this situation it should already be noted at this point that in particular when no significant movement has taken place between the capture operations the subtraction in question involves the captured projection images of the data sets themselves, but it is also conceivable to use projection images derived therefrom in the context of the subtraction, which will be described in more detail in the following.

The particular advantage of this first alternative embodiment is that no additional patient dose occurs during the capture of the mask data set because the latter does not actually show the patient, here specifically the head of the patient, but it is only the neurosurgical apparatus which is captured. Compared with the conventional methods in which the primary data set is captured as the single date set of projection images, no increase in the patient dose is consequently required.

In the workflow the neurosurgical apparatus, in particular a stereotactic frame, is therefore firstly already adjusted as well as possible to the patient. Then it is attached on a patient table of the X-ray device without the patient being present on said table. Thereafter the capture of the projection images of the mask data set ("mask scan") takes place, for example through rotation of the C-arm. In a further step the patient is then positioned as normal. Adjustments of the neurosurgical apparatus can be performed if required, whereupon the projection images of the primary data set are then captured with the patient in position.

Subsequently the logarithmic or linear subtraction of both data sets then takes place in the projection space which means that the subtraction can take place on the measured intensities or the logarithmized intensities, the latter being preferred because here the dependence on the specific capture parameters is no longer given but the standardized, logarithmized attenuation data of the projection images is considered. The possible truncation of the projection image data does not constitute a problem because the linearity of the Radon transform is taken into consideration. After the subtraction the reconstruction of the image data set takes place, which in this case shows only the head of the patient, wherein the artifacts should be significantly reduced or have disappeared entirely.

As has already been stated, on account of fairly small movements or readjustments of the neurosurgical apparatus it may well be the case that no perfect match exists between projection images of the same projection direction. Provision can then be made that, prior to the subtraction, projection images registered with one another of the primary data set and of the mask data set are defined. In this situation provision can specifically be made that in order to determine the registered projection images a portion, affecting at least one part of the neurosurgical apparatus, of three-dimensional reconstruction data sets determined from the primary data set and the mask data set are rigidly registered with one another. The basic concept of this embodiment is that the neurosurgical apparatus can in any case be sufficiently clearly recognized in the projection images of both data sets and consequently also in reconstruction data sets reconstructed therefrom that a registration can take place on this basis.

For this purpose, provision can specifically be made that in order to achieve rigid registration of the reconstruction data sets the neurosurgical apparatus in the reconstruction data set of the mask data set is segmented, a model of the neurosurgical apparatus is determined from the segmented neurosurgical apparatus, and at least one portion of the model is mapped in such a way into the reconstruction data set of the primary data set that as good a match as possible exists with the portion or the neurosurgical apparatus in the reconstruction data set of the primary data set. Because projection images of the mask data set ultimately show only the neurosurgical apparatus, a segmentation using known segmentation methods is conceivable, wherein for this purpose a prototype model of the neurosurgical apparatus or some other prior knowledge can advantageously already be taken into consideration. By this means it is for example also possible to differentiate artifacts or the like occurring in the reconstruction data set of the mask data set from actual features of the neurosurgical apparatus. In this situation, depending on the neurosurgical apparatus under consideration, said rigid registration may already be sufficient, which means that a transformation matrix is determined here between the reconstruction data set of the mask data set and the reconstruction data set of the primary data set by registering the model of the neurosurgical apparatus onto the similarly segmentable model of the neurosurgical apparatus in the reconstruction data set of the primary data set. One part of the model can already be sufficient in this situation in order to save on computational effort.

In particular in the situation when further settings have been made to the neurosurgical apparatus, in particular the fine adjustment of a stereotactic frame onto the patient, provision can be made that after the rigid registration has been determined an elastic registration is carried out in order to take into consideration displacements of the neurosurgical apparatus. Registration methods fundamentally known in the prior art can be employed both for the rigid registration and also for the elastic registration, and also for the purpose of segmentation in the reconstruction data sets known segmentation algorithms can be employed, here on account of the clear visibility of the neurosurgical apparatus in particular also threshold value based segmentation algorithms.

Furthermore, provision can then be made that the reconstruction data set of the mask data set adjusted by means of the registration onto the reconstruction data set of the primary data set is forward projected in order to determine projection images of the mask data set to be used in the context of the subtraction. Because the relationship between the reconstruction data sets is known, a corresponding rigid or where applicable elastic transformation onto the reconstruction data set of the mask data set can be applied, which means that new projection images registered with the projection images of the primary data set can be generated by means of forward projection, and ultimately therefore "virtual" mask projection images are produced which are then used in the context of the subtraction. In this way, motion effects between the captures of the primary data set and of the mask data set are taken into consideration and the subtraction and the following reconstruction of the image data set can be carried out.

Particularly advantageously, in the context of this first embodiment of the method it is also possible that a segmentation result for the neurosurgical apparatus in a three-dimensional reconstruction data set reconstructed from the captured projection images of the primary data set or of the mask data set is used in order to overlay at least one part of the stereoscopic apparatus, in particular at least one marker, into the image data set. If no movement whatsoever takes place, in particular any further adjustment, between the captures of the mask data set and of the primary data set, the reconstruction of the reconstruction data set preferably of the mask data set or of the primary data set takes place in addition, otherwise it is however possible to revert to the segmentation result in the context of the rigid or where applicable elastic registration in order to show at least a portion of the neurosurgical apparatus in the image data set and to complement this. In this situation, markers which can be associated with an in particular optical tracking system are preferably inserted into the image data set again, but this is also conceivable for instruments and the like used if guidance and/or navigation is to take place based on the image data set. Such an extended image data set is also expedient with regard to planning. Markers inserted into the image data set can for example be evaluated further for registration purposes with regard to a tracking system.

In a second alternative embodiment, provision may also be made that projection images of the head without the neurosurgical apparatus are captured as a mask data set, in which case at least one part of the projection image data of the mask data set and/or image data derived therefrom replaces, as attenuation data, projection image data of the captured projection images of the primary data set. In this second embodiment, the mask imaging cycle is carried out with the patient already fixed on the patient table of the X-ray device but without the neurosurgical apparatus, ideally with any movement of the patient being avoided during the imaging cycles for the mask data set and the primary data set. The mask data set can in this situation ultimately be employed as a type of "attenuation model" for correction of the projection image data. To this end, the projection image data (attenuation data) of the mask data set is used in order to complement projection image data of the primary data set at those positions where the neurosurgical apparatus is present. Actual measurement data is therefore used instead of the linear interpolation used in the prior art, with the correction also taking place again here in the projection image space.

The corrected projection images are then also utilized in this second embodiment in order to reconstruct a three-dimensional image data set without the neurosurgical apparatus. These, in particular a stereotactic frame and/or markers, can however also be inserted again here afterwards, which will be described in more detail in the following.

In a development of this second embodiment, provision can be made that mask pixels of the captured projection images of the primary data set, associated with the neurosurgical apparatus, are determined and the image data of these pixels is replaced by attenuation data of the projection images of the mask data set. In this situation the mask pixels can in turn be derived from a segmentation of the neurosurgical apparatus, which however preferably does not take place within the projection images of the primary data set, but provision is made in a particularly advantageous embodiment that the segmentation takes place in subtraction data obtained from the subtraction of projection image data of the primary data set and of the mask data set of corresponding projection directions or from three-dimensional reconstruction data sets derived from the primary data set and the mask data set, in which case when reconstruction data sets are used the mask pixels are obtained in the context of a forward projection of the segmentation result. The position of the neurosurgical apparatus in relation to the projection images can therefore easily be determined through subtraction of the two data sets, which means that the neurosurgical apparatus remains the only remaining object and a segmentation is consequently possible in a simple manner.

Because the capture of the primary data set and of the mask data set (except for the patient who is as motionless as possible) are essentially independent of one another, in order to reduce a patient dose provision can be made that the mask data set is captured at a reduced dose, in which case this can mean that fewer projection images are captured in total or a lower dose is used. For example, provision can be made that only one tenth of the projection directions which are used in the primary data set are used in the mask data set. Provision can consequently be made that projection images of the primary data set are captured at least in part using different projection directions than those of the mask data set and/or fewer projection images of the mask data set are captured than projection images of the primary data set. Provision can then expediently be made that attenuation data not present in one projection direction as captured projection image data of the mask data set is determined through interpolation in respect of the projection angle. It is therefore conceivable that missing projection images in the mask data set are so to speak reconstructed through interpolation, in particular in the situation when different capture protocols are used for the capture of the mask data set and the primary data set. For the purpose of interpolation, a linear interpolation or a spline interpolation can for example take place in respect of the projection angle characterizing the projection directions.

If however there is an appreciable movement of the patient, specifically therefore of the patient's head, between the capture of the mask data set and that of the primary data set, provision can thus also be made in the second embodiment that a registration takes place in respect of the patient between the primary data set and the mask data set. In particular, a similar procedure can be implemented here as in respect of the first embodiment, which means that a registration can also take place here between three-dimensional reconstruction data sets, wherein registered projection images can then be determined through forward projection.

Particularly advantageously, provision may also be made in the second embodiment that in the case of a segmentation of the neurosurgical apparatus in subtraction data obtained from the subtraction from the primary data set and the mask data set at least one part of the neurosurgical apparatus is overlaid into the image data set. It is consequently also possible in this embodiment to complement the image data set initially showing only the head of the patient with features of the neurosurgical apparatus because the latter is present in easily segmentable form in the subtraction data, in particular a three-dimensional subtraction-reconstruction data set. The image data set can thus be complemented with information regarding the neurosurgical apparatus which is necessary and/or meaningful in the context of the planning and/or support for an intervention.

As already mentioned, it is possible in both alternative forms of embodiment to have available three-dimensional data in respect of the head (in the form of the image data set) and three-dimensional data in respect of the neurosurgical apparatus. In this connection it is particularly expedient to employ dual volume representation techniques for the purpose of visualization. In this situation different three-dimensional data sets, here the image data set and a three-dimensional data set of the neurosurgical apparatus, are mixed together, in which case the mixing parameters can be suitably chosen. For example, the different three-dimensional volumes or elements segmented therein can be represented in different colors and the like. A particularly expedient representation is thus possible.

In addition to the method, an X-ray device is provided, in particular an X-ray device having a C-arm, on which are arranged opposite one another a radiation source and a radiation detector. The X-ray device comprises a control unit which is designed for carrying out the described method. Such X-ray devices which may also be employed in the context of neurosurgical interventions on account of the good movability of the C-arm and the fact that the latter occupies relatively little space are fundamentally known and can be designed through appropriate extension of the control unit so as to be used for carrying out the method. Suitable hardware and/or software components can be used for this purpose. All embodiments in respect of the method may be applied by analogy to the X-ray device, with which X-ray device the advantages given may consequently also be maintained.

BRIEF DESCRIPTION OF THE DRAWINGS

Further advantages and details will emerge from the exemplary embodiments described in the following and with reference to the drawings.

FIG. 1 shows a basic schematic diagram of a neurosurgical apparatus and a head,

FIG. 2 shows a flowchart of the first exemplary embodiment of the method,

FIG. 3 shows a schematic diagram of the basic principle of the first embodiment, FIG. 4 shows a flowchart of a second exemplary embodiment of the method.

DETAILED DESCRIPTION OF INVENTION

Figure 5:
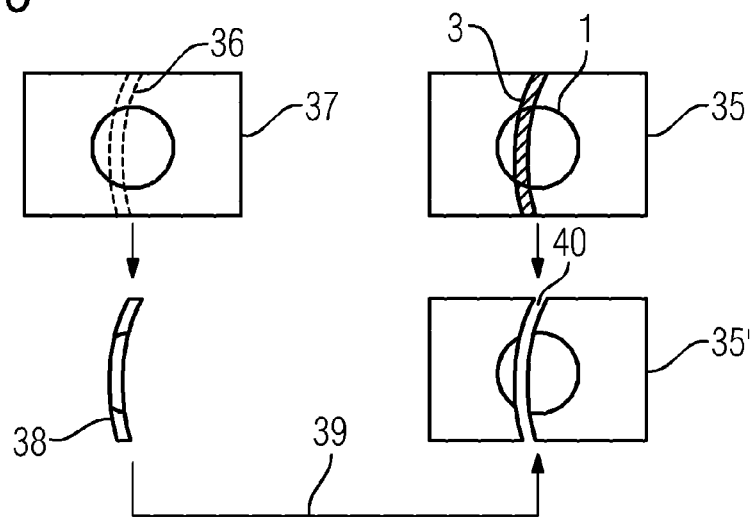
FIG. 5 shows a schematic diagram of the principle of the second embodiment.

FIG. 1 shows a basic schematic diagram of a scene which is the subject of the image capture using an X-ray device according to the described method. A neurosurgical intervention, in particular a minimally invasive intervention, is to be carried out on a patient whose head 1 according to FIG. 1 is already situated on a patient table 2 of the X-ray device.

In order to offer reliable guidance for minimally invasive instruments, for example a puncture needle, in order to maintain the position of the head as exactly as possible a stereotactic frame 3 which is fixed on the patient table 2 is provided here as the neurosurgical apparatus. The head 1 can be fixed, by means of adjustable fixing means 4, in the frame 3 which can naturally consist of a plurality of elements. The frame 3 also has a guide, not shown here in more detail for the sake of clarity, for the minimally invasive instrument.

Furthermore, arranged on the frame 3 are X-ray opaque markers 5 which are locatable using an optical tracking system. Because further components of the stereotactic frame 3, in particular the frame pieces, are also made of metal they also exhibit very little permeability to X-ray radiation. For that reason alone artifacts can arise due to the stereotactic frame 3 and the markers 5 when a three-dimensional reconstruction data set is calculated from a plurality of projection images captured using different projection directions. Added to this, however, is the fact that the imaging area of the X-ray device, the X-ray device in question having a C-arm, is not necessarily able to capture the complete arrangement shown in FIG. 1 in each projection image which means that in particular in respect of the stereotactic frame truncated projection images are produced, which can lead to further artifacts.

The correction of these artifacts is a primary objective of the method, which means that three-dimensional image data sets of the head 1 also suitable in particular for diagnostic and/or planning purposes can be maintained in spite of the use of neurosurgical apparatuses.

Two exemplary embodiments will be illustrated in detail here, corresponding to the first and second embodiments of the method discussed above.

FIG. 2 shows a basic flowchart of a first exemplary embodiment according to the first embodiment of the method.

The stereotactic frame 3 which is already adjusted as well as possible to the head 1 is initially arranged on the patient table 2 without the patient. In a step 6, under the same capture conditions and using the same capture parameters as later when capturing the projection images of the primary data set 7 in a step 8, capture then takes place of two-dimensional projection images of a mask data set 9, in which projection images consequently only the stereotactic frame 3 (with the markers 5) is contained.

Then in step 8 the patient is firstly positioned on the patient table 2, during which the stereotactic frame 3 remains motionless. Merely minor settings, consequently adjustments, of the stereotactic frame 3 to the head 1 are carried out before the capture of the primary data set which then shows the head 1 and the stereotactic frame 3 (with the markers 5) on its projection images also takes place in step 8. For each projection image of the primary data set 7 there exists a projection image of the mask data set 9 using the same projection direction.

Because minor movements can nevertheless occur between the capture of the primary data set 7 and the mask data set 9 as a result of the adjustments or other effects, a registration process is now initiated. To this end, in a step 10 three-dimensional reconstruction data sets 11, 12 are reconstructed both from the projection images of the mask data set 9 and also from the projection images of the primary data set 7, for example by using the filtered back projection method. In these reconstruction data sets 11, 12, in particular the reconstruction data set 11 of the mask data set 9, it is now possible relatively simply to segment the stereotactic frame 3, which happens in a step 13. In this situation prior knowledge about the stereotactic frame 3 can be taken into consideration and only a portion of the stereotactic frame 3 in particular not affected by the adjustment is considered. Segmentation results are obtained 14, 15 which can be regarded as models of the stereotactic frame 3 (or of the portion).

In a step 16, a registration of the reconstruction data sets 11, 12 now takes place in two steps, using the segmentation results 14, 15. A rigid registration thus takes place initially, based on the segmentation results 14, 15, whereupon in step 8 in order to take into consideration adjustments to the head 1 an elastic registration, in this case for the entire stereotactic frame 3 (with the markers 5), also takes place as a refinement. The result is a transformation which can correctly transform the reconstruction data set 11 of the mask data set into the coordinate system of the reconstruction data set 12, and the stereotactic frame 3 was consequently ultimately adjusted in the reconstruction data set 11 of the mask data set 9 to the stereotactic frame 3 in the reconstruction data set 12 of the primary data set 7. The result is a registered reconstruction data set 11 of the mask data set 9, from which in a step 17 can be derived projection images 18, registered by means of forward projection, of the mask data set 9.

In a step 19, the corresponding registered projection image 18 of the mask data set 9 is then subtracted from the corresponding projection image of the primary data set 7 for each projection direction. The results are subtraction images 20 for all the projection directions.

The principle of this approach is explained again in detail by means of the schematic diagram in FIG. 3. The arrow 22 in the left-hand partial image 21 symbolizes X-ray radiation which passes through the head 1 and the stereotactic frame 3. The partial image 21 thus symbolizes the attenuation described by the attenuation data of the projection images of the primary data set 7.

The center partial image 23 symbolizes the attenuation during the capture of the mask data set 9, where only the stereotactic frame 3 is present. If the subtraction is now carried out, the result for the subtraction images 20 according to partial image 24 is that the attenuation due to the stereotactic frame 3 ceases and then only the attenuation due to the head 1 remains.

It is consequently possible, step 25 in FIG. 2, to determine from the subtraction images 20 a three-dimensional image data set 26 solely of the head 1 with reduced artifacts due to the stereoscopic frame 3, or even none at all, for example again using filtered back projection.

However, since it is also frequently desired for planning, navigation and other support purposes to consider at least the markers 5, where applicable however also parts of the frame 3, simultaneously with the image data set 26, the segmentation results 14, 15 and/or the registered reconstruction data set 11 can be utilized in order to at least partially overlay the stereotactic frame 3, in particular the markers 5, into the three-dimensional image data set 26 and to represent this in a step 27. It is however preferred to generate a second three-dimensional volume containing the stereotactic apparatus 3 with the markers 5 and to use a dual volume representation by mixing with the image data set 26 in order to enable a yet more intuitive representation. A wide range of options is obviously conceivable here for providing a user with better quality three-dimensional views, freed from artifacts or at least significantly artifact-reduced, of the head 1 and at least partially of the neurosurgical apparatuses used.

FIG. 4 shows a flowchart of the second exemplary embodiment of the method which corresponds to the second embodiment. In this situation the same elements are identified by the same reference characters for the sake of simpler presentation.

A mask data set 9' is also captured in the second exemplary embodiment in a step 6', except that here at the time of capture in step 6' solely the head 1 is situated on the patient table 2 but not the stereotactic apparatus 3 with the markers 5. The projection images of the mask data set 9' consequently show only the head 1.

The patient is now not moved and the stereotactic frame 3 is attached and appropriately adjusted so that in a step 8 the primary data set 7 can be captured again, the projection images of which show the head 1 and the stereotactic frame 3 (with the markers 5).

In this situation it should be noted here that for the sake of simplified presentation a registration to be established where applicable on the basis of the head 1 or its anatomical features between the projection images of the mask data set 9' and of the primary data set 7 is not explained in detail here but can take place by analogy with the first embodiment if a movement of the head 1 has occurred.

In order to keep the radiation dose as low as possible for the patient, only one tenth of the projection images of the primary data set 7 were captured for the mask data set 9' in step 6'. An interpolation in respect of the projection angle therefore now firstly takes place in a step 28 in order to determine projection images for the missing projection directions and to obtain a completed mask data set 9'. In this situation, the interpolation can be linear or a spline interpolation can take place.

In a step 29, for each projection direction the respective projection image of the mask data set 9' is now subtracted from the projection image of the primary data set 7 with the result that subtraction data 30 is also produced here which now contains only the attenuation values in respect of the stereotactic frame 3 (with the markers 5). It is consequently possible in a step 31 to segment the stereotactic frame 3 there, which can happen in the subtraction images themselves but also in a three-dimensional reconstruction data set which is optionally to be calculated.

The results are ultimately mask pixels 32 which specify in which pixels of the projection images of the primary data set 7 attenuation components of the stereotactic frame 3 are present. The optional step 33 for determining a reconstruction data set from the subtraction data 30 and for segmentation in the reconstruction data set, whereupon the mask pixels 32 are determined by means of a forward projection, is only suggested in FIG. 4.

In a step 34, projection image data of the projection images of the primary data set 7 is then replaced for all the mask pixels 32 by projection image data of the projection images of the mask data set 9', with the result that the mask data set 9' ultimately acts as an attenuation model which makes available measurement data uninfluenced by neurosurgical apparatuses. This will be explained in detail with reference to the basic schematic diagram in FIG. 5.

The head 1 and a part of the stereotactic frame 3 can be recognized in an exemplary projection image 35 of the primary data set 7. The hatched region thus corresponds to mask pixels which are taken from the projection image 35 with the intention of forming a projection image 35'. At the same time the location 36 of the mask pixels in a projection image 37 of the mask data set 9' is known, which means that these can be cut out there, cf. detail 38. These now replace, arrow 39, the gap 40.

The result of step 34 is consequently a basic data set 41 with projection images which relate only to the head 1. From these, the three-dimensional image data set 26 can then in turn be defined in a step 25.

It is also possible in this second embodiment to determine in the image data set 26 complementable data relating to the stereoscopic frame 3 and in particular to the markers 5 by evaluating the subtraction data 30, which actually relates only to the stereoscopic frame 3 with the markers 5, correctly in order to determine a three-dimensional volume. A visualization can in turn accordingly take place in the step 27.

Figure 6:
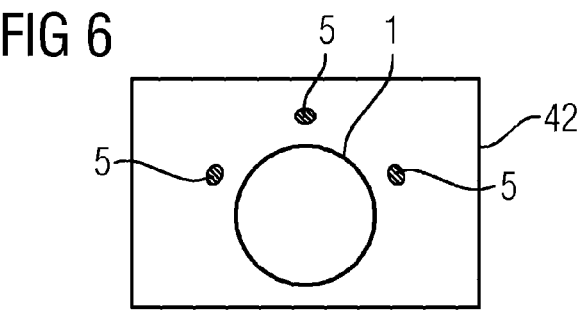
FIG. 6 shows a schematic diagram visualizing the image data set and FIG. 7 shows an X-ray device.

A possible visualization for both embodiments is suggested in FIG. 6. There the head 1 can be seen in a sectional view 42. In the context of a dual volume representation, markers 5 have been mixed in, positionally accurately, and also represented in a different color.

Figure 7:
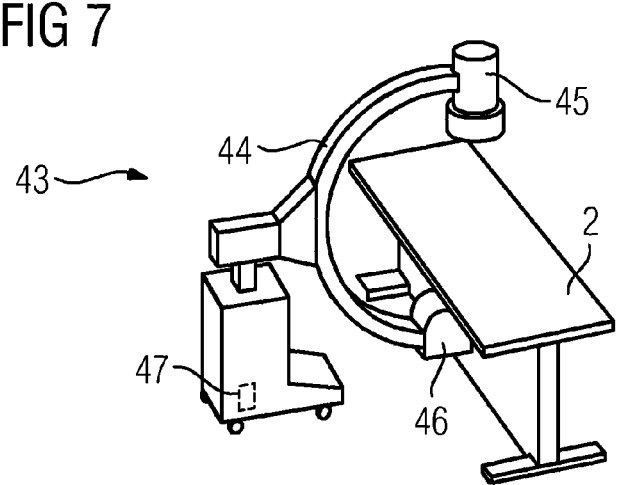

Finally, FIG. 7 shows a basic schematic diagram of an X-ray device 43. In addition to the patient table 2, this has a C-arm 44, on which are arranged opposite one another a radiation source 45 and a radiation detector 46. The C-arm 44 can be rotated in order to capture projection images in different projection directions. The operation of the X-ray device 43 is controlled by a control unit 47 which is designed so as to carry out the method as described, for example according to FIG. 2 or according to FIG. 4. This is where the calculations needed in order to obtain the artifact-reduced or artifact-free image data set 26 take place.

While specific embodiments have been described in detail, those with ordinary skill in the art will appreciate that various modifications and alternative to those details could be developed in light of the overall teachings of the disclosure. For example, elements described in association with different embodiments may be combined. Accordingly, the particular arrangements disclosed are meant to be illustrative only and should not be construed as limiting the scope of the claims or disclosure, which are to be given the full breadth of the appended claims, and any and all equivalents thereof. It should be noted that the term "comprising" does not exclude other elements or steps and the use of articles "a" or "an" does not exclude a plurality.

The invention claimed is:

1. A method for determining an artifact-reduced three-dimensional reconstructed image data set, comprising:
capturing projection images of a primary data set with different projection directions using an X-ray device, wherein the projection images of the primary data set show a head of a patient together with a neurosurgical apparatus having x-ray opaque markers, wherein the neurosurgical apparatus is fixed on a patient table and generates artifacts in a three-dimensional reconstruction,
capturing projection images of a mask data set, wherein the projection images of the mask data set show the neurosurgical apparatus without the head of the patient or show the head of the patient without the neurosurgical apparatus,
correcting the artifacts of the projection images of the primary data set using the projection images of the mask data set,
subtracting projection images of the primary data set and the mask data set from one another in a corresponding projection direction to determine subtraction images,
reconstructing an image data set from the subtraction images comprising only the head of the patient,
reconstructing a three-dimensional reconstruction data set from the projection images of the primary data set or of the mask data set,
segmenting the neurosurgical apparatus with the x-ray opaque markers in the three-dimensional reconstruction data set to obtain a segmentation result,
generating a second three-dimensional reconstruction data set from the segmentation result comprising only the neurosurgical apparatus with the x-ray opaque markers, and
dual volume representing the image data set from the subtraction images comprising only the head of the patient with the second three-dimensional reconstruction data set from the segmentation result comprising only the neurosurgical apparatus with the x-ray opaque markers, wherein the x-ray opaque markers are positionally mixed in the dual volume representation and represented in a different color.

2. The method as claimed in claim 1, wherein the head of the patient or the neurosurgical apparatus is held motionless between the capturing of the projection images of the mask data set and the capturing of the projection images of the primary data set.

3. The method as claimed in claim 1, wherein the projection images of the mask data set of the neurosurgical apparatus are adjusted to the head of the patient and are captured before the projection images of the primary data set are captured.

4. The method as claimed in claim 1, wherein, prior to the subtraction, projection images of the primary data set and of the mask data set are registered with one another.

5. The method as claimed in claim 4, wherein, in order to determine registered projection images, a portion, affecting at least one part of the neurosurgical apparatus, of three-dimensional reconstruction data sets determined from the primary data set and the mask data set are rigidly registered with one another.

6. The method as claimed in claim 5,
wherein, in order to achieve rigid registration of the three-dimensional reconstruction data sets, the neurosurgical apparatus in a reconstruction data set of the mask data set is segmented, wherein a model of the neurosurgical apparatus is determined from the segmented neurosurgical apparatus, and
wherein at least one portion of the model is mapped into a reconstruction data set of the primary data set such that a match exists with the at least one part of the neurosurgical apparatus or the neurosurgical apparatus in the reconstruction data set of the primary data set.

7. The method as claimed in claim 6, wherein after the rigid registration, an elastic registration is carried out in order to take into consideration displacements of the neuro surgical apparatus.

8. The method as claimed in claim 6, wherein the reconstruction data set of the mask data set is adjusted by a registration onto the reconstruction data set of the primary data set and is forward projected in order to determine projection images of the mask data set to be used for the subtraction.

9. The method as claimed in claim 1, wherein projection images of the head without the neurosurgical apparatus are captured as a mask data set, wherein at least one part of the projection image data of the mask data set and/or image data derived therefrom replaces, as attenuation data, projection image data of the projection images of the primary data set.

10. The method as claimed in claim 9, wherein mask pixels of the projection images of the primary data set, associated with the neurosurgical apparatus, are determined and wherein image data of the mask pixels are replaced by the attenuation data of the projection images of the mask data set.

11. The method as claimed in claim 10, wherein the mask pixels are derived from a segmentation of the neurosurgical apparatus.

12. The method as claimed in claim 11, wherein the segmentation takes place in subtraction data obtained from the subtraction of projection image data of the primary data set and of the mask data set of corresponding projection directions or from three-dimensional reconstruction data sets derived from the primary data set and the mask data set, wherein, when reconstruction data sets are used, the mask pixels are obtained during a forward projection of the segmentation.

13. The method as claimed in claim 9,
wherein the projection images of the primary data set are captured with different projection directions compared to projection directions of the mask data set and/or
wherein fewer projection images of the mask data set are captured than projection images of the primary data set,
wherein attenuation data, which are not present in one projection direction as projection image data of the mask data set, are determined by interpolation in respect of a projection angle.

14. The method as claimed in claim 9, wherein, during a segmentation of the neurosurgical apparatus within subtraction data obtained from the subtraction from the primary data set and the mask data set, at least one part of the neurosurgical apparatus is overlaid into the reconstructed image data set.

15. The method as claimed in claim 9, wherein a registration with respect to the patient takes place between the primary data set and the mask data set.

16. An X-ray device, comprising:
a C-arm that:
    captures projection images of a primary data set with different projection directions using an X-ray device, wherein the projection images of the primary data set show a head of a patient together with a neurosurgical apparatus having x-ray opaque markers, wherein the neurosurgical apparatus is fixed on a patient table and generates artifacts in a three-dimensional reconstruction, and
    captures projection images of a mask data set, wherein the projection images of the mask data set show the neurosurgical apparatus without the head of the patient or show the head of the patient without the neurosurgical apparatus, and
a control unit configured to:
    subtract projection images of the primary data set and the mask data set from one another in a corresponding projection direction to determine subtraction images,
    reconstruct an image data set from the subtraction images comprising only the head of the patient,
    reconstruct a three-dimensional reconstruction data set from the projection images of the primary data set or of the mask data set,
    segment the neurosurgical apparatus with the x-ray opaque markers in the three-dimensional reconstruction data set to obtain a segmentation result,
    generate a second three-dimensional reconstruction data set from the segmentation result comprising only the neurosurgical apparatus with the x-ray opaque markers, and
    dual volume represents the image data set from the subtraction images comprising only the head of the patient with the second three-dimensional reconstruction data set from the segmentation result comprising only the neurosurgical apparatus with the x-ray opaque markers,
    wherein the x-ray opaque markers are positionally mixed in the dual volume representation and represented in a different color.

* * * * *